US009522161B2

(12) United States Patent
Ferrante et al.

(10) Patent No.: US 9,522,161 B2
(45) Date of Patent: *Dec. 20, 2016

(54) PERFORMANCE ENHANCING COMPOSITION AND METHOD OF DELIVERING NUTRIENTS

(71) Applicant: Advanced Bio Development, Inc., Piermont, NY (US)

(72) Inventors: Ralph Mario Ferrante, Upper Grandview, NY (US); Chad Kevin Cunningham, Tappan, NY (US)

(73) Assignee: Advanced Bio Development, Inc., Piermont, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/668,087

(22) Filed: Mar. 25, 2015

(65) Prior Publication Data

US 2015/0196579 A1 Jul. 16, 2015

Related U.S. Application Data

(63) Continuation-in-part of application No. 13/238,483, filed on Sep. 21, 2011, now Pat. No. 8,999,424, which is a continuation-in-part of application No. 12/911,925, filed on Oct. 26, 2010, now abandoned.

(51) Int. Cl.

| | |
|---|---|
| A23L 1/30 | (2006.01) |
| A23K 1/175 | (2006.01) |
| A23L 2/00 | (2006.01) |
| A23L 2/38 | (2006.01) |
| A61K 31/7076 | (2006.01) |
| A61K 31/122 | (2006.01) |
| A61K 31/7004 | (2006.01) |
| A61K 31/522 | (2006.01) |
| A61K 31/047 | (2006.01) |
| A23L 2/02 | (2006.01) |
| A23L 2/39 | (2006.01) |
| A23L 2/395 | (2006.01) |
| A23L 2/44 | (2006.01) |
| A23L 2/52 | (2006.01) |
| A23L 2/56 | (2006.01) |
| A23L 2/58 | (2006.01) |
| A23L 2/66 | (2006.01) |
| A23L 2/68 | (2006.01) |

(52) U.S. Cl.
CPC .............. *A61K 31/7076* (2013.01); *A23L 2/02* (2013.01); *A23L 2/39* (2013.01); *A23L 2/395* (2013.01); *A23L 2/44* (2013.01); *A23L 2/52* (2013.01); *A23L 2/56* (2013.01); *A23L 2/58* (2013.01); *A23L 2/66* (2013.01); *A23L 2/68* (2013.01); *A23L 5/40* (2016.08); *A23L 5/51* (2016.08); *A23L 27/00* (2016.08); *A23L 29/00* (2016.08); *A23L 29/30* (2016.08); *A23L 33/10* (2016.08); *A23L 33/15* (2016.08); *A23L 33/16* (2016.08); *A23P 10/10* (2016.08); *A23P 10/20* (2016.08); *A61K 31/047* (2013.01); *A61K 31/122* (2013.01); *A61K 31/522* (2013.01); *A61K 31/7004* (2013.01); *A23V 2002/00* (2013.01)

(58) Field of Classification Search
CPC ........ A61K 9/0095; A61K 9/08; A61K 33/00; A23L 1/29; A23L 1/293; A23L 1/304
USPC .............................. 426/2, 541, 74, 590, 648
See application file for complete search history.

(56) References Cited

U.S. PATENT DOCUMENTS

| | | | |
|---|---|---|---|
| 5,547,942 A | 8/1996 | Rapaport | |
| 5,550,166 A | 8/1996 | Ostlund et al. | |
| 5,827,896 A | 10/1998 | Ostlund et al. | |
| 6,518,318 B1 | 2/2003 | Weeks | |
| 6,723,737 B1 | 4/2004 | Rapaport | |
| 7,160,565 B2 | 1/2007 | Rifkin | |
| 7,629,329 B2 | 12/2009 | Lee et al. | |
| 7,671,038 B1 | 3/2010 | Rapaport | |
| 2002/0110632 A1 | 8/2002 | Nunes et al. | 426/590 |
| 2003/0212134 A1 | 11/2003 | Dykstra | |
| 2004/0071825 A1 | 4/2004 | Lockwood | 426/72 |
| 2004/0234626 A1 | 11/2004 | Gardiner et al. | |
| 2006/0153899 A1 | 7/2006 | Kneller | 424/439 |
| 2008/0063689 A1 | 3/2008 | Farber | |
| 2008/0319076 A1 | 12/2008 | Kneller | 514/564 |
| 2010/0124587 A1 | 5/2010 | Heuer et al. | |
| 2010/0151023 A1 | 6/2010 | Beggan | |

OTHER PUBLICATIONS

Agteresch et al., "Adenosine triphosphate: established and potential clinical applications." Drugs. Aug. 1999; 58(2):211-32. (Abstract only).
Backhouse et al., "The influence of water ingestion during prolonged exercise on affect." Appetite, Mar. 2007; 48(2):193-8. (Abstract only).
Berardi et al., "Effects of Ribose Supplementation on Repeated Sprint Performance in Men", Journal of Strength and Conditioning Research, 2003, 17(1), 47-52.
Burke, "Caffeine and sports performance." Appl. Physiol. Nutr. Metab., Dec. 2008; 33(6):1319-34 (Abstract only).
Carvil et al., "Magnesium and Implications on Muscle Function." 2010 Strength & Conditioning Journal: Feb. 2010—vol. 32—Issue 1—pp. 48-54 (Abstract only).

(Continued)

*Primary Examiner* — Lien T Tran
*Assistant Examiner* — Tynesha McClain-Coleman
(74) *Attorney, Agent, or Firm* — White & Case LLP

(57) ABSTRACT

An aqueous composition specifically adapted for supporting physical performance. The liquid composition comprises, consists of, or consists essentially of ribose, a saccharide such as glucose or dextrose, coenzyme Q10, ATP, caffeine, and D-pinitol in conjunction with minerals and electrolytes. The orally-consumed liquid composition may be sold as a shelf-stable ready-to-drink liquid, or as a liquid concentrate or in solid form, such as a powder, granulate, or tablet to be added to water or other fluid. The liquid composition physiologically enhances essential energy stores and provides a supply of ingredients which support physiological generation and regeneration of ATP.

14 Claims, No Drawings

(56) References Cited

OTHER PUBLICATIONS

Casa et al., "Influence of Hydration on Physiological Function and Performance During Trail Running in the Heat", Journal of Athletic Training, 2010; 45(2):147-156.
Dang et al., "D-Pinitol and myo-Inositol Stimulate Translocation of Glucose Transporter 4 in Skeletal Muscle of C57BL/6 Mice", Biosci. Biotechnol, Biochem., 74 (5), 1062-1067, 2010.
Desbrow et al., "The effects of different doses of caffeine on endurance cycling time trial performance", J. Sports Sci. 2012; 30(2):115-20 (Abstract only).
Gul et al., "Oxidative stress and antioxidant defense in plasma after repeated bouts of supramaximal exercise: the effect of coenzyme Q10." J. Sports. Med. Phys. Fitness., Jun. 2011; 51(2):305-12. (Abstract only).
Gutierrez et al., "Reversal of muscle fatigue in intact rabbits by intravenous potassium chloride." J. Crit. Care., Dec. 1996; 11(4):197-205. (Abstract only).
Haff et al., "Carbohydrate supplementation and resistance training." J. Strength Cond. Res., Feb. 2003; 17(1):187-96. (Abstract only).
Hillman et al., "Exercise-induced dehydration with and without environmental heat stress results in increased oxidative stress." Appl. Physiol. Nutr. Metab., Oct. 2011; 36(5):698-706. (Abstract only).
Jeukendrup, "Carbohydrate intake during exercise and performance." Nutrition, vol. 20, Issue 7, pp. 669-677, Jul. 2004 (Abstract only).
Kim et al., "Synergistic antiinflammatory effects of pinitol and glucosamine in rats." Phytother. Res, Dec. 2005; 19(12):1048-51. (Abstract only).
Nassis et al., "Effect of water ingestion on cardiovascular and thermal responses to prolonged cycling and running in humans: a comparison", Eur. J. Appl. Physiol., Dec. 2002; 88(3):227-34. (Abstract only).
Nielsen et al., "Effects of high-intensity intermittent training on potassium kinetics and performance in human skeletal muscle." J. Physiol. 554.3 pp. 857-870. Feb. 2004.
Orstenblad et al., "Enhanced sarcoplasmic reticulum $Ca^{2+}$ release following intermittent sprint training." Am. J. Physiol. Regulatory Integrative Comp. Physiol. 279: R152-R160, 2000.
Paik et al., "Fluid replacement following dehydration reduces oxidative stress during recovery." Biochem. Biophys. Res. Commun. May 22, 2009; 383(1):103-7. (Abstract only).
Rathmacher et al., "Adenosine-5'-triphosphate (ATP) supplementation improves low peak muscle torque and torquefatigue during repeated high intensity exercise sets." Journal of the International Society of Sports Nutrition 2012, 9:48.
Rosenmeier et al., "Activation of ATP/UTP-selective receptors increases blood flow and blunts sympathetic vasoconstriction in human skeletal muscle." J. Physiol. 586.20 (2008) pp. 4993-5002.
Sharp, "Role of sodium in fluid homeostasis with exercise." J. Am. Coll. Nutr. Jun. 2006; 25(3 Suppl):231S-239S. (Abstract only).
Sivakumar et al., "Impact of D-pinitol on the attenuation of proinflammatory cytokines, hyperglycemia-mediated oxidative stress and protection of kidney tissue ultrastructure in streptozotocin-induced diabetic rats." Chem. Biol. Interact. Oct. 6, 2010; 188(1):237-45 (Abstract only).
Spriet et al., "Caffeine and Exercise Performance." ASCM Current Comment, 1996.
Temesi et al., "Carbohydrate Ingestion during Endurance Exercise Improves Performance in Adults", American Society for Nutrition, Mar. 16, 2011.
Van Loon et al., "Maximizing postexercise muscle glycogen synthesis: carbohydrate supplementation and the application of amino acid or protein hydrolysate mixtures." Am. J. Clin. Nutr. 2000; 72:106-11.
Verberg et al., "Loss of potassium from muscle during moderate exercise in humans: a result of insufficient activation of the Na+-K+-pump?" Acta Physiol. Scand. Apr. 1999; 165(4):357-67. (Abstract only).

Von Duvillard et al., "Fluids and hydration in prolonged endurance performance." Nutrition. Jul.-Aug. 2004; 20(7-8):651-6. (Abstract only).
Abe et al., "Effect of coenzyme Q10 in patients with mitochondrial myopathy, encephalopathy, lactic acidosis, and stoke-like episodes (MELAS): evaluation by noninvasive tissue oximetry." J. Neurol Sci. 1999, 162(1):65-8. (Abstract only).
Agteresch et al., "Beneficial effects of adenosine triphosphate on nutritional status in advanced lung cancer patients: a randomized clinical trial", J. of Olin. Oncol. vol. 20, No. 2, pp. 371-378, 2002.
Agteresch et al., "Pharmacokinetics of intravenous ATP in cancer patients", Eur. J. Clin. Pharmacol 56: 49-55, 2000.
Agteresch et al., "Randomized clinical trial adenosine 5'-triphosphate in patients with advanced non-small-cell lung cancer", J. of Nat. Cancer Inst., vol. 92, No. 4, 2000.
Ahlborg et al., "Carbohydrate utilization by exercising muscle following pre-exercise glucose ingestion", Clinical Physiol. and Functional Imaging, vol. 7, No. 3, p. 181-195, 2008.
Aoi et al., "Exercise and functional foods", Nutrition Journal, BioMed Central, 5:15, 2006.
Balsom et al., "Creatine in humans with special reference to creatine supplementation", Sports Medicine: 1994 (Abstract only).
Bannwarth et al., "A randomized, double-blind, placebo controlled study of oral adenosine triphosphate in subacute low back pain", J. of Rheumatology 32:6, 2005.
Barbiroli et al., "Coenzyme Q10 improves mitochondrial respiration in patients with mitochondrial cytopathies. An in vivo study on brain and skeletal muscle by phosphorus magnetic resonance spectroscopy." Cell Mol Biol 1997, 43(5): 741-9. (Abstract only).
Barr et al., "Nutritional Considerations for Vegetarian Athletes." Nutrition 20:696-703, 2004.
Bates et al., "Insulin-like effect of pinitol", Br. J. of Pharmacology, 130, 1944-1946, 2000.
Bell et al., "Effect of Repeated Caffeine Ingestion on Repeated Exhaustive Exercise Endurance", Med. & Sci. in Sports & Exercise, pp. 1348-1354, 2003.
Bemben, MG et al., "Creatine supplementation and exercise performance: recent findings" Sports Med. 2005;35(2): 107-25. (Abstract only).
Bendahan et al., "31 P NMR spectroscopy and ergometer exercise test as evidence for muscle oxidative performance improvement with coenzyme Q in mitochondrial myopathies." Neurology 1992, 42(6): 1203-8. (Abstract only).
Berchtold et al., "Calcium ion in skeletal muscle its crucial role for muscle function, plasticity, and disease", Physiological Reviews, vol. 80, No. 3, p. 1215, Jul. 2000.
Berube-Parent et al., "Effects of encapsulated green tea and Guarana extracts containing a mixture of epigallocatechin-3-gallate and caffeine on 24 h energy expenditure and fat oxidation in men", British J. of Nutrition, 94, p. 432-436, 2005.
Bhagavan et al., "Coenzyme Q10: Absorption, tissue uptake, metabolism and.pharmacokinetics." Free Radical Research 2006, 40(5): 445-453.
Body Action online, "D-pinitol", BodyActive online, www.bodyactive-online.co.uk, 2006.
Bodybuilding.com, "A new dietary supplement ingredient . . . to increase ATP and energy levels, . . . " retrieved from www.bodybuilding.com on Jul. 22, 2011.
Bodybuilding.com, "Is there a difference between the various forms of creatine?" posted Mar. 17, 2006.
Brault, et al, J. Appl Physiol 91;231-238, 2001.
Bresolin et al., "Clinical and biochemical correlations in mitochondrial myopathies treated with coenzyme Q10." Neurology 1988, 38(6): 892-9. (Abstract only).
Buford et al., "Glycine-Arginine-&-Ketoisocaproic Acid Improvs. Performance of Repeated Cycling Sprints." Medicine & Science in Sports & Exercise (2004) 583-587.
Buford et al., "International Society of Sports Nutrition position stand: creatine supplementation and exercise" Journal of the International Society of Sports Nutrition 2007, 4:6.
Calfee et al., "Popular Ergogenic Drugs and Supplements in Young Athletes. Pediatrics Official Journal of the American Academy of Pediatrics." Pediatrics 2006;117;e57-e589.

(56) References Cited

OTHER PUBLICATIONS

Camic et al., "Effects of arginine-based supplements on the physical working capacity at the fatigue threshold." J Strength Cond. Res. May 2010;24(5):1306-12. (Abstract only).
Campbell et al., "Pharmacokinetics, safety, and effects on exercise performance of I-arginine a-ketoglutarate in trained adult men." Nutrition 22 (2006) 872-881.
Campbell et al., "The Ergogenic Potential of Arginine." Journal of the International Society of Sports Nutrition. 1(2):35-38, 2004.
Cheetham et al., "Human muscle metabolism during sprint running." J Appl. Physiol. Jul. 1986; 61(1); 54-60. (Abstract only).
Chen et al., "ATP Release Guides Neutrophil Chemotaxis via P2Y2 and A3 Receptors," Science, 2005.
Conley et al., "Oxidative capacity and ageing in human muscle," J. of Physiology, 526.1, pp. 203-210, 2000.
Cooke et al., "Effects of acute and 14-day coenzyme Q10 supplementation on exercise performance in both trained and untrained individuals," Journal of the International Society of Sports Nutrition 2008, 5:8.
Cooper-Douglas Laboratories, "Ultra Cardio CoQ10 Cardiovascular support," 2007.
Cordain et al., "Does creatine supplementation enhance athletic performance", Journal of the American College of Nutrition, vol. 17, No. 3, 205-206, 1998.
Costill et al., "Carbohydrate nutrition and fatigue", PubMed, Sports Med. 13(2):86-92, 1992.
Davis et al., "Caffeine and anaerobic performance: ergogenic value and mechanisms of action", Sports Med. 2009; 39(10):813-32.
Davis et al., "Effect of pinitol treatment on insulin action in subjects with insulin resistance", Diabetes Care, vol. 23, No. 7, Jul. 2000.
Deitrich et al., "Red blood cell regulation of microvascular tone through adenosine triphosphate," Am J Physiol Heart Circ Physiol, 278:H1294-1298, 2000.
Dhar et al., "Cardiovascular Toxicities of Performance-Enhancing Substances in Sports." Mayo Clin. Proc., Oct. 2005;80(10)1 307-1315.
Dodd et al., "The role of ribose in human skeletal muscle metabolism," Medical Hypotheses, 62, pp. 819-824, 2004.
Doherty et al., "Effects of caffeine ingestion on rating of perceived exertion during and after exercise: a meta-analysis," Scand J Med Sci Sports, 15, pp. 69-78, 2005.
Echegaray et al., "Blood glucose responses to carbohydrate feeding prior to exercise in the heat: effects of hypohydration and rehydration", Int. J. Sport Nutr. Exerc. Metab. 11(1): 72-83, 2001.
Ellsworth, "Red blood cell-derived ATP as a regulator of skeletal muscle perfusion," Medicine & Science in Sports & Exercise, pp. 35-41, 2004.
Febbraio et al., "Effects of carbohydrate ingestion before and during exercise on glucose", J. Appl. Physiol. 89:2220-2226, 2000.
Ferrante et al., "Tolerance of high-dose (3,000 mg/day) coenzyme Q10 in ALS." Neurology 2005, 13;65(11): 1834-6. (Abstract only).
Fisher-Wellman, "Acute exercise and oxidative stress a 30 year history", Dynamic Medicine, 8:1, 2009.
Folkers et al., "Biochemical rationale and the cardiac response of patients with muscular", Pro. Natl. Acad. Sci, USA, vol. 82, pp. 4512-4516, Jul. 1985.
Folkers et al., "Therapy with coenzyme Q10 of patients in heart failure who are eligible or ineligible for a transplant." Biochem Biophys Res Commun. 1992, 182(1): 247-53. (Abstract only).
Forrester et al., "Effect of Adenosine Triphosphate and Some Derivatives on Cerebral Blood Flow and Metabolism," J Phusiol, 296, pp. 343-355, 1979.
Franco-Obregon, "Is serum a hoax?" www.creatine-blog.com, Apr. 2005.
Fu et al., "Antifatigue effect of coenzyme Q10 in mice." J Med Food 2010, 13(1):211-5. (Abstract only).
Fujimoto et al., "Effects of coenzyme Q10 administration on pulmonary function and exercise performance in patients with chronic lung diseases." Clin Investig. 1993, 71(8 Suppl): S 162-6. (Abstract only).
Gallagher et al., "Effects of ribose supplementation on adenine nucleotide concentration", Official Journal of the American College of Sports Medicine, vol. 33, No. 5, Suppl. 2001.
Gleeson et al., "Comparison of the effects of pre-exercise feeding of glucose, glycerin", European Journal of Applied Physiology, vol. 55, No. 6, 645-653, 1986 (Abstract only).
Goda et al., "Clinical Improvement after administration of coenzyme Q10 in a patient with mitochondrial encephalomyopathy." J Neurol. 1987, 234(1): 62-3. (Abstract only).
Gökbel et al., "The effects of coenzyme Q10 supplementation on performance during repeated bouts of supramaximal exercise in sedentary men." J Strength Cond Res. 2010, 24(1): 97-102. (Abstract only).
Goldstein et al., "International Society of Sports Nutrition Position Stand: Caffeine and Performance," J of the Intel. Society of Sports Nutrition, 7:5, 2010.
Gonzalez et al., "Erythrocyte and the Regulation of Human Skeletal Muscle Blood Flow and Oxygen Delivery, Role of Circulating ATP," American Heart Asso. pp. 1046-1055, 2002.
Graham et al., "Does caffeine alter muscle carbohydrate and fat metabolism during exercise?" Appl. Physiol. Nutr. Metab. 33: pp. 1311-1318, 2008.
Grant et al., "Therapeutic nutraceutical treatments for osteoarthritis and ischaemia." Exp. Opin. Ther. Patents (2000) 10(1).
Green et al., "Carbohydrate ingestion augments skeletal muscle creatine accumulation during creatine supplementation in humans." Am. J. Physiol. Nov. 1996;271(5 Pt 1):E821-6. (Abstract only).
Greenberg et al., "Co-enzyme Q10: a new drug for cardiovascular disease." J Clin Pharmacol 1980, 30(7): 596-608. (Abstract only).
Greenwood et al., "Differences in Creatine Retention Among Three Nutritional Formulations of Oral Creatine Supplements." Journal of Exercise Physiologyonline; vol. 6 No. 2 May 2003.
Greenwood et al., "D-Pinitol Augments Whole Body Creatine Retention in Man." Journal of Exercise Physiologyonline; vol. 4 No. 4 Nov. 2001.
Gross et al., "Metabolism of D-ribose administered continuously to healthy persons and to patients with myoadenylate deaminase deficiency" Klin Wochenschr. Dec. 4, 1989;67(23):1205-13.
Gross et al., "Ribose Administration during Exercise: Effects on Substrates and Products of Energy Metabolism in Healthy Subjects and a Patient with Myoadenylate Deaminase Deficiency." Klinische Wochen-schrift,1991 (69), 151-155.
Gundling et al., "Complementary and alternative medicine in cardiovascular disease: what is the evidence it works?" Dept, of Internal Med. Uni. of Cal. at Davis, vol. 171, p. 191, 1999.
Harris et al., "The creatine content of Creatine Serum and the change in the plasma concentration with ingestion of a single dose." Journal of Sports Sciences, vol. 22; Sep. 9, 2004, pp. 851-857 (Abstract only).
Hellsten "Urate uptake and Urate uptake and lowered ATP levels in human muscle after high-intensity intermittent exercise", Am J Physiol Endocrinol Metab 274:600-606, 1998.
Hellsten et al., "AMP deamination and purine exchange in human skeletal muscle during and after intense exercise." Journal of Physiology (1999), 520.3, pp. 909-920.
Hellsten et al., "Antioxidant supplementation enhances the exercise-induced increase in mitochondrial uncoupling protein 3 and endothelial nitric oxide synthase mRNA content in human skeletal muscle." Free Radic Biol Med. 2007, 43(3): 353-61. (Abstract only).
Hellsten et al., "Effect of ribose supplementation on resynthesis of adenine nucleotides after intense intermittent training in humans." Am J Physiol Regul Integr Comp Physiol. Jan. 2004; 286(1):R182-8. (Abstract only).
Hellsten-Westing et al., "Decreased resting levels of adenine nucleotides in human skeletal muscle after high-intensity training." 1993 the American Physiological Society.
Hogervorst et al., "Caffeine improves physical and cognitive performance during exhaustive exercise," The American College of Sports Medicine, pp. 1841-1851, 2008.
Hopwood et al., "Creatine Supplementation and Swim Performance: Brief Review" Journal of Sports Science and Medicine (2006) 5, 10-24.

(56) References Cited

OTHER PUBLICATIONS

Horleys et al., "Fact sheet creatine dietary supplement", Horleys Intellgent Sports Nutrition, www.horleys.com. 2008.
Hudson et al., "Effects of caffeine and aspirin on light resistance training performance, perceived exertion, and pain perception," J. Strength Cond. Res., Nov. 2008, (22) 6, 1950-7 (Abstract only).
Humanetics, Effect of pinitol administration on type II diabetics, retrieved from www.humanetics.com on Feb. 11, 2011.
Humanetics, Glucose transport and muscle glycogen, retrieved from www.humanetics.com on Feb. 11, 2011.
Humanetics, Mechanism of action how inzitol works to manage glucose, retrieved from www.humanetics.com on Feb. 11, 2011.
Humanetics, Preclinical research, retrieved from www.humanetics.com on Feb. 11, 2011.
Ihara et al., Mitochondrial encephalomyopathy (MELAS): pathological study and successful theraphy with coenzyme Q10 and idebenone. J Neurol Sci. 1989, 90(3): 263-71. (Abstract only).
Jacobson et al., "Effect of caffeine co-ingested with carbohydrate or fat on metabolism and performance in endurance-trained men," Exp. Physiol. 86.1, pp. 138-144, 2011.
JingQing, "Clinical observation of oral adenosine triposthate in treating rhinitis medicamentosa," Chi Med J. 113(4):349, 2000.
Jordan et al., "Effects of oral ATP supplementation on anaerobic power and muscular strength," Med Sci Sport Exer, pp. 983-990, 2004.
Jung et al., "Influence of Hydration and Electrolyte Supplementation on Incidence and Time to Onset of Exercise-Associated Muscle Cramps." Journal of Athletic Training, 2005;40(2);71-75, © by the National Athletic Trainers' Association, Inc.
Kaikkonen et al., "Coenzyme Q10: absorption, antioxidative properties, determinants and plasma levels." Free Radical Research 2002, vol. 36, No. 4, pp. 389-397. (Abstract only).
Kaikkonen et al., "Effect of oral coenzyme Q10 supplementation on the oxidation resistance of human VLDL+LDL fraction: absorption and antioxidative properties of oil and granule-based preparations." Free Radical Biology & Medicine 1997, vol. 22, No. 7, pp. 1195-1202. (Abstract only).
Keen et al., "Dietary magnesium intake influences exercise capacity and ematologic", Metabolism, 36(8):788-93, 1987.
Kerksick et al., "The Effects of Creatine Monohydrate Supplementation With and Without D-Pinitol on Resistance Training Adaptations." Journal of Strength and Conditioning Research vol. 23(9)2673-2682 (Dec. 2009).
Kichenin et al., "Cardiovascular and pulmonary response to oral administration of ATP in rabbits," J Appl. Physiol, 88: 1962-1968, 2000.
Kichenin et al., "Chronic oral administration of ATP modulates nucleoside transport and purine metabolism in rats," J of Pharm. and Exp. Therap. vol. 294, No. 1, pp. 126-133, 2000.
Kon et al., "Effect of Coenzyme Q10 supplementation on exercise-induced muscular injury of rats." 2007.
Kon et al., "Reducing exercise-induced muscular injury in kendo athletes with supplementation of coenzyme Q10." Br J Nutr. 2008, 100(4): 903-9. (Abstract only).
Koyama et al., "Suppressive effect of coenzyme Q10 on phospholipase A2 activation in cardiac cells after prolonged swimming." Life Sci. 1992, 51(14): 1113-8. (Abstract only).
Kraemer et al., "Compatibility of high-intensity strength and endurance training on hormonal and skeletal muscle adaptations", Center for Sports Medicine, The Penn. State Univ., p. 976, 1995.
Kraemer et al., "Effects of a multi-nutrient supplement on exercise performance and hormonal response to resistance exercise." Eur. J. Appl. Physiol. (2007).101:637-646.
Kreider et al., "Creatine supplementation analysis of ergogenic value, medical safety, and concerns", JEP online, vol. 1, No. 1, 1998.
Kreider et al., "ISSN exercise & sport nutrition review: research & recommendations," Sports Nutrition Review Journal, 1(1):1-44, 2004.
Kreider et al., "Long-term creatine supplementation does not significantly affect clinical markers of health in athletes." Molecular and Cellular Biochemistry 244; 95-104, 2003.
Kwong et al., "Effects of coenzyme Q10 administration on its tissue concentrations, mitochondrial oxidant generation, and oxidative stress in the rat." Free Radio Biol Med. 2002, 1;33(5): 627-38. (Abstract only).
Landbo et al., "Interaction between warfarin and coenzyme Q10." Ugeskr Laeger 1998, 160(22): 3226-7. (Abstract only).
Langsjoen et al., "A six year clinical study of therapy of cardiomyopathy with coenzyme Q10." Int J Tissue React 1990, 12(3): 169-71. (Abstract only).
Langsjoen et al., "Introduction to coenzyme Q10", retrieved from http://faculty.washington.edu/ely/coenzq10.html on Jun. 3, 2008.
Langsjoen et al., "Overview of the use of CoQ10 in cardiovascular disease." Biofactors, 1999; 9(2-4):273-84. (Abstract only).
Langsjoen et al., "Pronounced increase of survival of patients with cardiomyopathy when treated with coenzyme Q10 and conventional therapy." Int J Tissue React. 1990; 12(3):163-8. (Abstract only).
Leeuwenburgh et al., "Oxidative Stress and Antioxidants in Exercise." Current Med. Chem. 2001, 8:829-838.
Leij-Halfwerk et al., "Adenosine triphosphate infusion increases liver energy status in advanced lung cancer patients: an in vivo $^{31}$P magnetic resonance spectroscopy study," Hepatology, vol. 35, No. 2, 2002.
Linden et al., "Cell biology: purinergic chemotaxis," Science 314, pp. 1689-1690, 2006.
Littarru et al., "Biomedical and clinical aspects of coenzyme Q", Clin. Investig 587-588, 1993.
Lulinkski et al., "Creatine supplementation", Quackwatch.org// creatine.html, 1999.
Malinauskas et al., "Supplements of interest for sport-related injury and sources of . . . ," Advances in Medical Sciences, ISSN 1096-1126, vol. 52, p. 50, 2007.
Maridakis et al., "Caffeine attenuates delayed-onset muscle pain and force loss following eccentric exercise," The J of Pain, vol. 8, No. 3, pp. 237-243, 2007.
Matsumoto et al., "Branched-Chain Amino Acid Supplementation Increases the Lactate Threshold during an Incremental Exercise Test in Trained Individuals." J. Nutr. Sci. Vitaminol, 55, 52-58, 2009.
Maughan, "Nutritional ergogenic aids and exercise performance." Nutrition Research Reviews (1999), 12, 255-280.
McCartney et al., "Muscle power and metabolism in maximal intermittent exercise." J Appl Physiol. Apr. 1986;60(4):1164-9. (Abstract only).
McDowall, "Supplement use by young athletes", J. of Sports Science and Medicine, 6, 337-342, 2007.
McNaughton et al., "Effects of chronic bicarbonate ingestion on the performance of high-intensity work", Eur. J. Appli. Physiol. Occup. Physiol., 80(4):333-6, 1999 (Abstract only).
McNaughton et al., "Sodium bicarbonate can be used as an ergogenic aid in high-intensity, competitive cycle ergometry of 1 h duration", Eur. J. Appl. Physiol. Occup. Physiol., 80(1):64-9, 1999.
McNaughton et al., "Ergogenic effects of sodium bicarbonate", Curr. Sports Med. Rep., 7(4):230-6, 2008.
Mizuno et al., "Antifatigue effects of coenzyme Q10 during physical fatigue." Nutrition, 2008 24(4):293-9. (Abstract only).
Morrow, "How to improve athletic performance with arginine and grape seed extract?" www.jarretmorrow.com; May 5, 2010.
Nahas, "Complementary and alternative medicine approaches to blood pressure reduction", Canadian Family Physician, 54:1529-33, 2008.
Narayanan et al., "Pinitol—a new anti-diabetic compound from the leaves of Bougainvillea spectabilis," Current Science (1987) 56(3) 139-41 (Abstract only).
Nicholas et al., "Influence of ingesting a carbohydrate-electrolyte solution on endurance capacity during intermittent, high-intensity shuttle running", J. Sports Sci., 13(4):283-90, 1995.
Nishikawa et al., "Long-term coenzyme Q10 therapy for a mitochondrial encephalomyopathy with cytochrome c oxidase deficiency: a 31P NMR study." Neuology, 1989; 39(3):399-403. (Abstract only).

(56) References Cited

OTHER PUBLICATIONS

Nutros.com, "Nutritional supplement facts for d-pinitol", Nutritional Supplement Review, retrieved from ww.nutros.com on Jul. 14, 2010.
Ochs, "The effect of pinitol on the key aspects of carbohydrate metabolism in isolated muscle tissue and its interaction with insulin," Humanetics, The Science of Supplements, 2011.
Ohtani et al., "Amino Acid Mixture Improves Training Efficiency in Athletes." American Society of Nutrition (2006); 0022-3166/06.
Ohtani et al., "Amino Acid Supplementation Affects Hematological and Biochemical Parameters in Elite Rugby Players." Biosci. Biotechnol. Biochem., 65.(9), 1970-1976, 2001.
Omran et al., "D-Ribose improves diastolic function and quality of life in congestive heart failure patients: a prospective feasibility study." The European Journal of Heart Failure 5 (2003) 615-619.
Oopik et al., "Effects of sodium citrate ingestion before exercise on endurance performance in well trained college runners", Br. J. Sports Med, 37:485-489, 2003.
Ostrowski et al., "The effect of weight training volum on hormonal output and muscular size and function", J. Strength Cond. Res. (1997) (Abstract only).
Paddon-Jones et al., "Potential Ergogenic Effects of Arginine and Creatine Supplementation." American Society for Nutritional Sciences (2004) 0022-3166/04.
Pauly, et al., "D-Ribose as a Supplement for Cardiac Energy Metabolism." J. Cardovasc Pharmacol Therapeut 5(4):249-258, 2000.
PeakATP—Product Information (2005).
Pliml et al., "Effects of ribose on exercise-induced ischaemia in stable coronary artery disease." The Lancet Saturday Aug. 29, 1992 vol. 340 No. 8818 pp. 507-501.
Porter et al., "The effect of oral coenzyme Q10 on the exercise tolerance of middle-aged, untrained men." Int J Sports Med. 1995; 16(7):421-7. (Abstract only).
Preen et al., "Creatine supplementation: a comparison of loading and maintenance protocols on creatine uptake by human skeletal muscle." Int. J. Sport Nutr. Exerc. Metab. Mar. 2003;13(1):97-111. (Abstract only).
Quinn et al., "Creatine and athletic performance-sports supplements", retrieved from www.about.com on Nov. 27, 2007.
Rabini et al., "Diabetes mellitus and subjects' ageing: a study on the ATP content and ATP-related enzyme activities in human-erythrocytes," Euro. J. of Clin. Investigation, 27, pp. 327-332, 1997.
Rapaport et al., "Anticancer activities of adenine nucleotides in mice are mediated through expansion of erythrocyte ATP pools," Proc. Natl. Acad. Sci. USA, vol. 86, pp. 1662-1666, 1989.
Rasmussen et al., "Influence of D-pinitol on whole body creatine retention," Humanetics, 2011.
Ravada et al., "Synthesis of Coenzyme Q10." American Journal of Infectious Diseases, 2009; 5(2):83-89.
Robinson et al., "Role of submaximal exercise in promoting creatine and glycogen", J. Appl. Physiol., 87:598-604, 1999.
Rosenfeldt et al., "Coenzyme Q10 in the treatment of hypertension: a meta-analysis of the clinical trials." J Hum Hypertens. Apr. 2007;21(4):297-306. (Abstract only).
Rosenfeldt et al., "Systematic review of effect of Coenzyme Q10 in physical exercise, hypertension and heart failure." Biofactors. 2003;18(1-4):91-100.(Abstract only).
Rosenmeier et al., "Circulating ATP-induced vasodilatation overrides sympathetic vasoconstrictor activity in human skeletal muscle," J. Physiol 558.1, pp. 351-365, 2004.
Rossignol et al., "Measuring the contribution of pharmacological treatment to advice to stay active in patients with subacute low-back pain: a randomized controlled trial," Pharm. and Drug Safety, 2005.
Sawka et al., "Fluid and electrolyte supplementation for exercise heat stress." Am J Clin Nutr 2000;72(suppl);564S-72S. © 2000 American Society for Clinical Nutrition.
Scott et al., "Safety and efficacy assessment of oral pinitol in diet treated diabetic subjects," Humanetics (2004) retrieved from www.humanetics.com on Apr. 11, 2011.
Segal et al., "The metabolism of D-ribose in man," J Clin Invest. May 1958; 37(5): 719-735.
Seifert et al., "The effect of ribose ingestion on indices of free radical production", Free Radical Biol Med., 2002; 33 (Suppl 1): S269.
Selsby et al., "Swim Performance Following Creatine Supplementation in Division III Athletes." National Strength and Conditioning Association, © 2003 17(3):421-4.
Sherman et al., "Carbohydrate feedings 1 h before exercise improves cycling performance." Am J Clin Nutr 1991; 54:866-70, © 1991 American Society for Clinical Nutrition.
Shimomura et al., "Protective effect of coenzyme Q10 on exercise-induced muscular injury." Biochem Biophys Res. Commun. Apr. 15, 1991;176(1):349-55. (Abstract only).
Short et al., "Decline in skeletal muscle mitochondrial function with aging in humans," PNAS, vol. 102, No. 15, pp. 5618-5623, 2005.
Sims et al., "Preexercise sodium loading aids fluid balance and endurance for women", J. Appl, Physiol, 103:534-541, 2007.
Sims et al., "Sodium Loading Aids Fluid Balance and Redcues Physiological Strain of Trained Men Exercising in the Heat." Medicine & Science in Sports & Exercise, 2007, 123-130.
Skadhauge-Jensen et al., "Availability of Ribose Is Limiting for ATP Resynthesis in Human Skeletal Muscle After High-Intensity Training." Medicine & Science in Sports & Exercise: May 2001—vol. 33—Issue 5—p. S329. (Abstract only).
Sökmen et al., "Caffeine use in sports: considerations for the athlete," J Strength Cond. Res., 2008, 978-86. (Abstract only).
Spano, "Enhancing Athletic Performance," retrieved from www.foodproductdesign.com on Feb. 23, 2011.
Sprague et al., "ATP: the red blood cell link to NO and local control of the pulmonary circulation," The American Physiological Society, H2717, 1996.
Sprague et al., "Reduced expression of $G_i$ in erythrocytes of humans with type 2 diabetes is associated with impairment of both cAMP generation and ATP release," Diabetes, vol. 55, 2006.
St Cyr et al., "Enhanced high energy phosphate recovery with ribose infusion after global myocardial ischemia in a canine model." J. Surg. Res. Feb. 1989;46(2):157-62. (Abstract only).
Stathis et al., "Influence of sprint training on human skeletal muscle purine nucleotide metabolism." J. Appl. Physiol. Apr. 1994;76(4):1802-9. (Abstract only).
Steenge et al., "Protein and carbohydrate induced sugmentation of whole body creatine", J. Appl. Physiol, 89:1165-1171, 2000.
Steinberg, "Adenosine-5-monophosphate in venous insufficiency," Angiology, pp. 154-161, 1958.
Stevens et al., "High-intensity dynamic human muscle performance enhanced by a metabolic intervention." Medicine & Science in Sports & Exercise, Dec. 2000—vol. 32, Issue 12, 2000, pp. 2102-2108.
Stuart et al., "Multiple effects of caffeine on simulated high-intensity team-sport performance," The American College of Sports Med., pp. 1998-2005, 2005.
Tauler at al., "Supplementation with an antioxidant cocktail containing coenzyme Q prevents plasma oxidative damage induced by soccer." Eur. J. Appl. Physiol. Nov. 2008;104(5):777-85. (Abstract only).
Teitelbaum et al., "The Use of D-Ribose in chronic Fatigue Syndrome and Fibromyalgia: A Pilot Study." The Journal of Alternative and Complementary Medicine: vol. 12, No. 9, 2006, pp. 857-862.
Tokish et al., "Ergogenic Aids: A Review of Basic Science, Performance, Side Effects, and Status in Sports." Am. J. Sports Med. 2004; 32; 1543.
Tullson et al., "Adenine nucleotide synthesis in exercising and endurance-trained skeletal muscle." The American Physiological Society (1991) 0363-6143/91.
Van Gammeren et al., "The Effects of Four Weeks of Ribose Supplementation on Body Composition and Exercise Performance in Healthy, Young, Mail Recreational Bodybuilders: A Double-Blind, Placebo-Controlled Trial." Current Therapeutic Research vol. 63, No. 8, Aug. 2002.
Vollestad et al., "Effect of exercise intensity on potassium balance in muscle and blood of man", J. of Physiol. 475.2, pp. 359-368, 1994.

(56) References Cited

OTHER PUBLICATIONS

World Anti-Doping Code, 2011 Prohibited List (Sep. 2010).
Wagner et al., "Effects of Oral Ribose on Muscle Metabolism during Bicycle Ergometer in AMPD-Deficient Patients." Ann Nutr Metab, 1991; 35:297-302.
Wagner, et al., "McArdle's Disease: Successful Symptomatic Therapy by High Does Oral Administration of Ribose." Kiln Wochenschr (1991) 69:92.
Wang, "Clinical observation of oral adenosine triposthate in treating rhinitis medicamentosa," Chinese Medical Journal,113(4):349, 2000.
Weber, "Dietary Intake and Absorption of Coenzyme Q", Accessed on Jun. 30, 2010 from books.google.com.
Wilborn et al., "Effects of zinc magnesium aspartate (ZMA) supplementation on training", J. of Intern. Soci. Of Sports Nutrition 1(2):12-20, 2004.
Wilfert et al., "NCAA issues notice about nutritional-supplement provision", NCAA News Archive, 2005.
Yamamoto et al., "Mitochondrial myopathy, encephalopathy, lactic acidosis, and strokelike episodes with recurrent abdominal symptoms and coenzyme Q10 administration". Journal of Neurology, Neurosurgery, and Psychiatry 1987;50:1475-1481.
Ylikoski et al., "The effect of coenzyme Q10 on the exercise performance of cross-country skiers." Mol Aspects Med. 1997;18 Suppl:S283-90. (Abstract only).
Zarzeczny et al., "Influence of ribose on adenine salvage after intense muscle contrations", J. Appl. Physiol. 91:1775-1781, 2001.
Zenk et al., "A Prospective, randomized, double blind study to evaluate the effects of orally administered adenosine triphosphate on peripheral perfusion in adult men and women," 2005.
Zhang et al., "Uptake of Dietary Coenzyme Q Supplement Is Limited in Rats." American Institute of Nutrition. 1995 0022-3166.
Zheng et al., "Influence of CoQ10 on autonomic nervous activity and energy metabolism during exercise in healthy subjects" J. Nutr. Sci. Vitaminol (Tokyo). Aug. 2008;54(4):286-90. (Abstract only).
Zimmer, "Ribose Accelerates the Repletion of the ATP Pool During Recovery from Reversible lschemia of the Rat Myocardium." J. Med. Cell Cardiol. 16, 863-866, 1984.
Zöllner et al., "Myoadenylate Deaminase Deficiency: Successful Symptomatic Therapy by High Dose Oral Administration of Ribose." Klin Wochenschr (1986) 64:1281-1290.
Monosaccharide- & Fat-Free Foods, http://www.livestrong.com/article/491477-monosaccharide-fat-free-foods/ Jul. 13, 2011.
Absorption of Monosaccharides, http://www.vivo.colostate.edu/hbooks/pathphys/digestion/smallgut/absorb-sugars. html, Apr. 16, 2006.

PERFORMANCE ENHANCING COMPOSITION AND METHOD OF DELIVERING NUTRIENTS

This application is a continuation-in-part of U.S. patent application Ser. No. 13/238,483, filed on Sep. 21, 2011, now U.S. Pat. No. 8,999,424, which is a continuation-in-part of U.S. patent application Ser. No. 12/911,925, filed on Oct. 26, 2010, abandoned. The contents of each of these applications are incorporated herein by reference in their entirety.

I. BACKGROUND OF THE INVENTION

1. Field of the Invention

The present invention is directed to nutraceutical compositions which support physical performance, attenuate muscle fatigue, and enhance aerobic respiration utilization capacity. The composition may be prepared in the form of a ready-to-drink liquid composition, or a liquid concentrate or a tablet, granulate, powder, or other solid form to be added to water or other fluid to form a drinkable liquid at the time of ingestion. Advantageously, the inventive composition enhances physiologically vital energy stores and the bioavailability of adenosine triphosphate (ATP) energy reserves. The composition also provides for regeneration of ATP in skeletal muscle, enhances the delivery and uptake of glucose in skeletal muscle, and provides essential electrolytes and other ingredients to a consumer of the liquid composition.

More specifically, the present invention relates to a novel composition comprising, consisting of, or consisting essentially of ribose, a saccharide, ATP, coenzyme Q10, caffeine, and D-pinitol. The composition may also contain minerals and electrolytes to stimulate and enhance generation of ATP activity in the body.

2. Description of the Related Art

The human body derives energy from carbohydrates, fats and proteins during chemical processes within the cells. The energy released from these nutrients is used to form the nucleotide ATP. ATP is used to promote three major categories of cellular function: membrane transport, synthesis of chemical compounds, and mechanical work. As cells use ATP to perform work, the ATP is chemically broken down into a pool of nucleotides, most of which are re-aminated and re-phosphorylated back to ATP. When intense exercise is repeated frequently, as in training, there is an accumulated loss of nucleotides from the muscle. The restoration of the nucleotide pool occurs mainly through de novo synthesis but also through the re-use of intracellular purines through the purine salvage pathway.

Carbohydrates are the primary source of energy in human diets. Essentially all carbohydrates are converted into glucose before they reach the cell. Once glucose enters the cell, enzymes in the cytoplasm or the nucleoplasm convert the glucose into pyruvic acid through a process called glycolysis. This process produces a small amount of ATP, while 90 percent of ATP is formed in the mitochondria. Pyruvic acid and acetoacetic acid (from fatty and amino acids) are converted into acetyl coenzyme-A in the cytoplasm and transported into the mitochondrion. Here a series of enzymes act upon acetyl coenzyme-A, which undergoes dissolution through a sequence of chemical reactions known as the tricarboxylic acid cycle or Krebs cycle. As a result of these processes, one molecule of glucose forms a total of 38 molecules of ATP.

Low blood glucose or muscle glycogen levels during exercise contribute to fatigue. Maintaining or elevating body carbohydrate reserves may optimize exercise performance. Pre-exercise carbohydrate consumption has the potential to increase liver and muscle glycogen concentrations during the hours before exercise. Further, carbohydrates consumed prior to exercise may be absorbed via the small intestine during exercise and help maintain adequate blood glucose concentrations. Studies have shown a 15% increase in performance and a 13% improved endurance time to exhaustion with pre-exercise carbohydrate consumption. In some studies using carbohydrate solutions containing 200 g glucose per liter, performance was improved. Carbohydrate availability during exercise was greater and the pre-exercise carbohydrate consumption increased carbohydrate oxidation above normal amounts, thereby allowing a higher work rate during the later stages of exercise.

ATP is vital to cellular function. Energy from ATP is required for membrane transport of glucose and other essential substances, such as sodium ions, potassium ions, calcium ions, phosphate ions, chloride ions, urate ions, hydrogen ions, and many other substances. Membrane transport is so important to cellular function that some cells utilize nearly half the ATP formed in the cells for this purpose alone.

ATP also supplies the energy to promote synthesis of a great number of substances, including proteins, phospholipids, cholesterol, purines, and pyrimidines. Synthesis of almost any chemical compound requires energy. For example, in the formation of one molecule of protein, many thousands of ATP molecules are broken down to release energy. Cells utilize up to 75 percent of all the ATP formed in the cell to synthesize new chemical compounds, particularly during the growth phase of a cell.

ATP is also essential for muscle contraction. In skeletal muscle, calcium ions bind to the troponin complex, causing the tropomyosin to shift and thereby expose the myosin binding sites of the actin to the myosin heads. The myosin heads move the thin filament contracting the muscle, also called a power stroke. ATP provides the energy required for the myosin heads to release the actin and move back into place for another power stroke. The amount of ATP that is present in the muscle fiber is sufficient to maintain full contraction for less than one second. The ATP is broken down into adensosine diphosphate (ADP), which is rephosphorylated to form new ATP within a fraction of a second. The two main sources of energy to reconstitute ATP are foodstuffs, such as carbohydrates, fats and proteins, and creatine phosphate.

ATP exists both inside (intracellular) and outside (extracellular) virtually every cell of the body. The role of intracellular ATP has been well established. It is largely responsible for the energetics, function and survival of cells. When the phosphate bonds of ATP are broken down, the energy released helps to empower all body functions to occur. Extracellular ATP regulates many physiological responses, such as vascular, cardiac and muscle functions, by interacting with specific ATP receptors on cell surfaces. When intracellular ATP becomes depleted, extracellular ATP can cross into cells via its catabolic components, adenosine and inorganic phosphate.

Physical activity, specifically high-intensity or prolonged exercise, requires a high rate of ATP utilization as well as a rapid rate of regeneration. The regeneration rate exceeds the maximum capacity of the muscle, resulting in the accumulation of ADP and adenosine monophosphate (AMP) in the muscle. With further adenine nucleotide degradation, inosine monophosphate (IMP) forms and accumulates in the muscle. A fraction of IMP is further degraded to nucleotide bases that are released into the bloodstream, resulting in a decrease in total adenine nucleotides (TAN, ATP+ADP+AMP) contributing to an overall decrease in ATP.

A single period of exhaustive exercise of short duration can cause ATP levels in human skeletal muscle to drop temporarily to 60-70% of resting values, but ATP levels are restored to pre-exercise levels shortly after the exercise is ended. However, the loss of nucleotides from frequently-repeated exercise exceeds the rate of regeneration, causing ATP levels to remain below baseline levels. Studies have shown that intense exercise performed regularly over one to several weeks decreases concentrations of ATP resting levels by 15-20%.

Extracellular ATP is a major regulator of vascular, cardiac and muscle functions. By activating specific ATP receptors present on vascular endothelial cells (the cells that line the blood vessels walls), ATP improves blood vessel tone and increases vasodilation, which reduces pulmonary and systemic vascular resistance (the resistance of the vessels to blood flow). These actions stimulate blood flow to peripheral areas without affecting blood pressure or heart rate. Additionally, exogenous ATP enhances the delivery of glucose, nutrients and oxygen to working and recovering muscles as well as helping to remove catabolic waste products. These mechanisms improve physical performance, benefit muscle growth, strength and recovery, and increase overall energy levels. Increases in extracellular ATP have also been demonstrated to enhance cerebral blood flow and metabolism, thereby supporting mental acuity and potentially lessening the perception of fatigue and/or exercise-associated pain.

After ingestion, ATP is broken down into adenosine and inorganic phosphate. Following rapid absorption by the gut, these compounds are incorporated into and expand the body's liver ATP pools. Detailed experimental animal studies have demonstrated that the turnover of the expanded liver ATP pools supply the necessary precursor, adenosine, for red blood cell ATP synthesis. In sum, exogenously administered ATP elevates liver ATP pools, which in turn yields elevated red blood cell ATP pools. Subsequently, the expanded red blood cell ATP pools are slowly released into the blood plasma (extracellular). Animal and human studies have both conclusively shown that oral administration of ATP elevates ATP levels in liver, red blood cells and blood plasma.

Each molecule of ATP consists of three phosphate groups and one adenosine molecule, which itself is composed of an adenine ring and a ribose molecule. Ribose is a pentose sugar found in many essential biological molecules, such as all nucleotides, nucleotide coenzymes, all forms of RNA, and ATP. Ribose is a key component and a limiting factor in the creation and regeneration of ATP. Ribose supplementation in rats has been shown to increase nucleotide salvage three- to six-fold and hypoxanthine salvage six- to eight-fold, depending on muscle fiber type. Ribose supplementation in humans has also been shown to attenuate loss of TAN during chronic high-intensity exercise, and return TAN and ATP levels to baseline within 65 to 72 hours. In contrast, subjects without ribose supplementation remained at under 80% of resting TAN and ATP levels. When consumed orally, 88-100% of ribose is absorbed in the intestines within two hours.

Coenzyme Q10 (CoQ10), like ribose, exists in all cells and is integral to many vital biological activities. Such activities include a role as an essential antioxidant, supporting the regeneration of other antioxidants, influencing the stability, fluidity and permeability of membranes, stimulating cell growth, and inhibiting cell death. Additionally, CoQ10 has a fundamental role in cellular bioenergetics as a cofactor in the mitochondrial electron transport chain (respiratory chain), and is therefore essential for the production of ATP. The human body can synthesize CoQ10 as well as derive it from several food products, including meat, fish, peanuts and broccoli. The dietary intake of CoQ10 is about 2-5 mg per day, while the total amount of CoQ10 in the body of a normal adult is estimated to be approximately 0.5-1.5 g. Studies have shown that the uptake of CoQ10 into the blood is approximately 5 to 10% of the dose administered. Dosages of 90 to 150 mg/day have shown to increase plasma concentrations by 180%. Under certain conditions including oxidative stress, production of CoQ10 may not meet the body's demand. In several medical studies and studies of trained athletes, CoQ10 supplementation has been shown to provide enhanced cellular energy levels in cardiac performance by increasing respiratory chain activity, improving oxygen utilization during exercise, accelerating post-exercise recovery, decreasing heart rate during exercise, improving performance, and increasing mean power (the average rate at which work is performed or energy is converted). CoQ10 has also been used as a supplementary treatment for diseases such as Chronic Heart Failure (CHF), muscular dystrophies, Parkinson's disease, cancer, and diabetes.

Caffeine is a bitter, white crystalline xanthine alkaloid. It is quickly absorbed through the gastrointestinal tract. It is then metabolized by the liver and through enzymatic action results in three metabolites: paraxanthine, theophylline, and theobromine. It has been shown that elevated levels can appear in the bloodstream within 15 to 45 minutes of consumption, and peak concentrations are evident one hour post ingestion. Circulating concentrations are decreased by 50 to 75% within three to six hours of consumption. Caffeine crosses the membranes of nerve cells as well as muscle cells and it has been proposed that its effects may be more neural than muscular. It has also been proposed that caffeine may have more powerful effects at steps other than metabolism in the process of exciting and contracting the muscle. Research suggests that caffeine acts to decrease reliance on glycogen utilization and increases dependence on free fatty acid mobilization during exercise. It has also been shown that caffeine may improve endurance performance by increasing the secretion of β-endorphins and this may lead to a decrease in pain perception. Other studies indicate that caffeine significantly enhances neuromuscular function and/or skeletal muscle contraction. Caffeine consumption has been shown to promote a significant thermogenic response, namely, increasing energy expended.

Pinitol, a form of Vitamin B inositol, is a plant extract that has insulin-like properties without causing hypoglycemia and stimulates glucose uptake and glycogen synthesis in muscle cells. Chemically, it is defined as an inositol, a kind of sugar alcohol. Enhancing the efficiency of glucose utilization is beneficial as muscle cells more readily uptake glucose and either utilize it for energy or store it as glycogen. Increased glycogen levels in muscles will improve endurance and increase the fullness of muscles. Pinitol stimulates glucose uptake in muscle cells by 25-80%. D-pinitol appears to exert an acute and chronic insulin-like effect in mice that have a hypoinsulinemic type of diabetes. D-pinitol is able to exert this effect independent of insulin, and it appears D-pinitol is able to stimulate glucose transport into the cell via a "by-pass" mechanism that activates the glucose transport cascade distal to the normal activation via the insulin to insulin receptor interaction.

Electrolytes and minerals are crucial to increasing endurance and maintaining the body's physical capabilities during prolonged or highly-intense physical activity. Potassium and magnesium are known to play a major role in overcoming the effects of muscle fatigue. Substantial amounts of potassium and magnesium are lost from the contracting muscles during exercise, and there is a rapid decrease in plasma potassium after the cessation of exercise. A low extracellular potassium concentration can cause muscular weakness, changes in cardiac and kidney function, lethargy and even coma in severe cases. There are no reserves of potassium or sodium in the animal body, and any loss beyond the amount of intake comes from the body's own cells and tissues. The kidney is the key regulator of potassium and sodium. While the kidney can, with a low intake of sodium, reduce excretion thereof to a very low level to conserve the supply in the body, potassium is not so efficiently conserved.

Electrolytes are lost during physical activity through the process of hypotonic dehydration and isotonic dehydration, for example, through sweating or due to high ambient temperatures. The sodium concentration in sweat averages 35 mmol/L, while potassium, calcium and magnesium concentrations in sweat are 5, 1, and 0.8 mmol/L, respectively. Pre-exercise hydration with sodium and other electrolytes has been shown to decrease cardiovascular and thermal strain and enhance exercise capacity in trained and untrained men and women.

There are particular "energy drinks" on the market which purport to increase stamina and physical performance. These beverages generally contain various combinations of caffeine, electrolytes, sugars, juices, herbal extracts, and/or other components which act mainly as stimulants. However, none of these products are specifically designed for enhancing the biogeneration of ATP, nor do they include all the essential components parts of ATP generation or regeneration. Accordingly, there remains a need for a nutraceutical supplement composition which supports a biochemical ready source of cellular energy by promoting the biogeneration of ATP.

Applicants' application Ser. No. 12/911,925, filed on Oct. 26, 2010, is directed to a nutraceutical supplement composition comprising ribose, coenzyme Q10, a saccharide, creatine, and D-pinitol.

II. SUMMARY OF THE INVENTION

The present invention is directed to a nutraceutical supplement composition for enhancing physical performance by enhancing the bio-availability of ATP energy reserves and the resynthesis of ATP in human skeletal muscle. Advantageously, the inventive composition increases the delivery and uptake of glucose and stimulates the increase of ATP in skeletal muscle. The invention may also provide essential electrolytes and other ingredients to the consumer in order to support physical performance, attenuate muscle fatigue, and enhance aerobic respiration utilization capacity. The present invention can also be used as a nutritional supplement for human beings prior to physical activity. The present invention also provides a method for facilitating generation and regeneration of ATP lost by chronic, high-intensity or prolonged physical activity. The invention also provides a process for preparing the composition for oral consumption.

The nutraceutical supplement composition comprises, consists essentially of, or consists of ribose, coenzyme Q10, a saccharide, ATP, caffeine, and D-pinitol. The strategic biochemical effect of the present invention works to increase the generation and regeneration of ATP to support the body's ability to perform greater work. Specifically, the combination of the individual components provides a synergistically enhanced effect on ATP generation and regeneration. One aspect of the present invention is directed to an aqueous composition comprising, consisting of, or consisting essentially of the nutraceutical supplement composition for enhancing physical performance.

For ease of discussion, the inventive formulation will be termed a composition. It will be apparent from the surrounding text as to whether the composition is in the form of a ready-to-consume liquid formulation, a liquid concentrate, or in a solid form (such as, but not limited to, tablets, a powder, granulate, or solid concentrate), in which case the composition is mixed with water, juice, or other fluid to form an aqueous solution or mixture at the time of ingestion. Regardless of their physical form, the inventive compositions, whether in liquid or solid form, are stable for extended periods of time.

The term "about", when used in connection with any of the quantities or concentrations of a particular component in a formulation, is be understood as allowing a tolerance of ±10% of the given amount of that component, or in the tolerance of the upper and lower limits of the component. For example, if the concentration of a component in a composition is given as "about 10 grams per liter", the amount of that component in the composition is permitted to be 10 grams ±10%, or in the range of from 9 grams per liter to 11 grams per liter. Analogously, if a concentration range is given as "about 10 grams to about 100 grams per liter", the concentration of the component may range from 9 grams per liter (10 grams per liter minus 10%) to 110 grams per liter (100 grams per liter plus 10%).

Unless otherwise qualified, all compositions are to be understood as aqueous formulations in which the various components are dissolved or suspended in water. All of the ingredients do not need to be completely solubilized, and some of the components can be suspended in the fluid and consumed in a non-homogeneous state. Any of the formulations of the invention may have components which are solubilized and/or partly solubilized. A concentration of a component (e.g. 1 gram per liter) is to be understood as the concentration of that component in the final ready-to-consume formulation. Depending upon the particular embodiment of the invention, other aqueous liquids such as juice (e.g. apple juice, orange juice, cranberry juice), tea (e.g. prepared green tea or black tea), or coffee can be used to dissolve or suspend the components in place of (or in addition to) water.

Although the inventive compositions are stable for extended periods of time, in particular embodiments of the invention, it may be desirable to keep particular components of the composition physically separated from other ingredients until shortly prior to ingestion. For example, to maximize product shelf life, efficacy, or potency, it may be useful to maintain certain ingredients in a dry form until just prior to consumption while the remaining ingredients are dissolved in a bulk liquid formulation.

In such embodiments, the container, such as a bottle or pouch, may have a specially designed storage compartment or closure to keep particular ingredients dry and separated from the remaining ingredients. Just prior to consumption, a dispensing mechanism can be activated to dispense the separated component(s) into the liquid beverage, for example, using a closure-activated mechanism, shortly before consumption. Advantageously, such a dispensing system extends the product's shelf life by keeping components which may be affected by long-term contact with moisture in a solid form and away from any liquid. Containers with dispensing mechanisms for solid components are known in the art, for example, VIZcap dosing and dispensing bottle caps, from VIZ Enterprises LLC (Atlanta, Ga.). In an exemplary embodiment, dry ingredients, such as ATP, caffeine, coenzyme Q10, or D-pinitol may be packaged in the dry storage compartment and the remaining ingredients can be dissolved in the bulk formulation. Such embodiments will depend upon the particular formulation and implementation of the invention, as well as any marketing goals.

The concentrations of the various components will generally vary within predetermined ranges to provide the desired degree of supplementation to the body. For example, in certain embodiments of the invention, the concentrations of the various components in liquid form can vary within the following ranges:

ribose: about 25 grams to about 83.3 grams per liter;
coenzyme Q10: about 16.6 milligrams to about 5 grams per liter;
saccharide: about 16.6 grams to about 333.3 grams per liter;
ATP (as ATP disodium) about 16.6 milligrams to about 16.6 grams per liter;
Caffeine: about 416.6 milligrams to about 5 grams per liter; and
D-pinitol: about 16.6 milligrams to about 16.6 grams per liter.

All the indicated concentrations refer to concentrations in the prepared ready-to-consume liquid composition.

The saccharide can conveniently be glucose or dextrose, although other easily-absorbable saccharides such as sucrose, fructose, or galactose are within the scope of the present invention.

For ease of discussion, all such liquid formulations of the inventive composition will be considered as "ready-to-consume" or "ready-to-use" and shelf-ready units. Alternatively, the components can be maintained in dry form as a concentrate or powder, and added to water or fluid shortly prior to ingestion. The components can also be in the form of a liquid concentrate to be diluted with water or other fluid before consumption.

In addition to containing ribose, coenzyme Q10, a saccharide, ATP, caffeine, and D-pinitol, the nutraceutical composition may optionally further contain one or more minerals or electrolytes. These minerals or electrolytes may be selected from the group consisting of sodium, potassium, calcium, and magnesium. In further embodiments, additional minerals or vitamins can be added for further supplementation. The minerals may be in the form of conventional biologically-acceptable salts, such as chlorides, carbonates, and citrates. For ease of discussion, the minerals or electrolytes will be referred to without counterion, although it will be understood the minerals will be in the form of a biologically acceptable salt or other compound. The minerals and electrolytes can have multiple purposes. For example, a sodium salt (such as sodium benzoate) can be both a source of sodium and a preservative.

For example, if the nutraceutical composition contains sodium, potassium, calcium, and/or magnesium as minerals or electrolytes, the concentrations of these components in the final liquid form can vary within the following ranges:

sodium: about 16.6 milligrams to about 5 grams per liter;
potassium: about 16.6 milligrams to about 3.3 grams per liter;
calcium: about 16.6 milligrams to about 1.6 grams per liter; and
magnesium: about 16.6 milligrams to about 1.6 grams per liter.

All of the weights of any metallic minerals or electrolytes in the composition refer to weights of the metal itself in the composition, and not to the weights of any constituent salts.

The nutraceutical composition may further optionally contain a preservative to maintain the quality of the product. The preservative can be a commercially-available substance with known preservation properties, such as sodium chloride, sodium citrate, sodium benzoate, or a mixture of these or other preservatives.

The water content of the liquid nutraceutical composition will be sufficient to give the desired effective concentration ranges for the various components. In one embodiment, the water content may be in the range of from about 800 to about 900 grams per liter of prepared beverage. When the composition is sold in solid form or as a liquid concentrate, the packaging will provide specific instructions as to the amount of water (or other liquid) to be added.

The composition may also contain an acidulant to adjust the pH to a desired pH level, for example, to provide acidity for stability of the components, or tartness for a satisfying taste sensation. The acidulant can be any known or commercially-available biologically-acceptable acidifying substance. For example, the acidulant can be selected from the group consisting of citric acid, lactic acid, maleic acid, tartaric acid, and combinations thereof, and the pH can be adjusted to about 3 to about 6.5, or any other, particular biologically-acceptable value.

The composition may also optionally contain common flavoring and/or coloring ingredients to provide a particular taste or appearance. These flavors or colors can be natural or synthetic, and may be added in accordance with techniques known in the art. For example, the resultant composition may contain flavorings such as kiwi, pomegranate, green tea lemonade, mixed berry, tropical citrus, or blueberry. It will be understood that any of the flavoring agents and colorants in any of the disclosed formulations can be exchanged with any other flavoring agents or colorants. In addition, flavor modifiers such as flavor masking agents can be used to adjust the taste of the formulations to suit a particular flavor profile. The flavoring agent may also be a juice such as apple juice, grape juice, or lemon juice; a tea such as brewed green tea, black tea, or herbal tea; coffee such as brewed coffee or coffee extract; or other flavoring agent known in the art.

Certain components of the composition may have multiple functions, such as but not limited to preservatives, sources of electrolytes, and/or acidulants. The various components of the liquid composition do not need to be completely dissolved, and the composition may be consumed in the form of a suspension, emulsion or other non-homogeneous mixture. Any undissolved solid material will generally be minimal and will still be absorbed by the body.

One embodiment of the invention directed to a nutraceutical composition for enhancing physical performance comprises, consists of, or consists essentially of the following components per liter in liquid form:

ribose: about 25 grams to about 83.3 grams
coenzyme Q10: about 16.6 milligrams to about 5 grams
saccharide: about 16.6 grams to about 333.3 grams
ATP (as ATP disodium) about 16.6 milligrams to about 16.6 grams
Caffeine: about 416.6 milligrams to about 5 grams
D-pinitol: about 16.6 milligrams to about 16.6 grams
sodium: about 16.6 milligrams to about 5 grams
potassium: about 16.6 milligrams to about 3.3 grams
calcium: about 16.6 milligrams to about 1.6 grams magnesium: about 16.6 milligrams to about 1.6 grams
a preservative; and
an acidulant.

Another embodiment of the invention is directed to a nutraceutical liquid composition for enhancing physical performance. The composition comprises, consists of, or consists essentially of the following components having the indicated concentrations per liter in liquid form:

glucose: about 15 grams to about 340 grams;
ribose: about 25 grams to about 85 grams;
coenzyme Q10: about 15 milligrams to about 5 grams;
ATP (as ATP disodium): about 15 milligrams to about 17 grams
caffeine: about 415 milligrams to about 17 grams;
D-pinitol: about 15 milligrams to about 17 grams;
sodium: about 15 milligrams to about 5 grams;
potassium: about 15 milligrams to about 3.5 grams;
calcium: about 15 milligrams to about 2 grams;
magnesium: about 15 milligrams to about 2 grams;
a preservative; and
an acidulant.

In a preferred embodiment of the invention, the nutraceutical composition comprises, consists of, or consists essentially of the following components per liter in liquid form:

ribose: about 25 to about 83.3 grams
coenzyme Q10: about 1.5 grams to about 5 grams
ATP (as ATP disodium) about 1.6 grams to about 12.5 grams
Caffeine about 833.3 milligrams to about 3.3 grams
D-pinitol: about 250 milligrams to about 8.3 grams
saccharide: about 167 to about 300 grams
sodium: about 1 gram to about 3.5 grams
potassium: about 420 milligrams to about 2.5 grams
calcium: about 170 milligrams to about 1 gram;
magnesium: about 80 milligrams to about 1 gram;
a preservative; and
an acidulant The composition may be sold as a shelf-stable ready-to-drink bottled liquid. When sold as a ready-to-drink liquid, the consumer can simply open the container and ingest the liquid as with any conventional beverage. The novel composition may also be sold as a liquid concentrate, or in the form of a tablet, powder, granulate, ready-to-dissolve dry concentrate, or similar dry formulation for reconstitution by the consumer. Methods for making such tablet, powder, granulate, or other solid formulations as well as liquid concentrates are readily known to the person of ordinary skill in the art. The dry composition can be sold in individual units such as tablets, sachets, stick-packs, concentrates, or in bulk multi-dose packages. Liquid concentrates can be sold as sachets, stick packs, or the like. The components of the liquid concentrate may be dissolved and/or suspended in the concentrate. The dry solid compositions and the concentrate formulations may be readily reconstituted by the consumer by adding a predetermined quantity of water (or other fluid such as juice, carbonated water, soda, tea, or coffee) to the solid or concentrate shortly before consumption, or the reverse by adding the solid or concentrate to the fluid. After mixing, the formulation is ready for consumption. The amount of liquid added to solid or concentrate formulations of the composition is not critical as long as the components are sufficiently dissolved and/or suspended in a fluid for convenient consumption. Consumers may wish to make the reconstituted formulation more dilute or more concentrated in accordance with their taste preferences.

In tabletted embodiments, the composition may comprise binders, lubricants, disintegrants, and/or other known tablet excipients. These tabletting excipients can be added to the other components of the composition during blending. Other solid formulations may also contain known excipients to improve flow, absorb moisture, or reduce degradation to provide for a satisfactory customer experience. Proportions of ingredients for the solid formulations are generally the same as for the ready-to-drink formulations.

The concentrate can also be sold in "shot" packs, bottles, or other containers. For example, the manufacturer can sell a 60 ml, 100 ml, or other-sized bottle containing the dry powder composition, and the consumer would simply add a pre-determined amount of water or other fluid to the bottle and shake the contents. The bottles can be single-use or reusable, depending on the manufacturer's preference and marketing plans.

Another aspect of the invention is directed to a method of enhancing physiologically essential energy stores in human skeletal muscle. The method comprises administering an effective amount of the novel composition to a subject in need thereof.

The liquid composition can be consumed at any time to enhance the consumer's ability to generate and regenerate ATP levels. For example, the composition can be consumed 30 minutes to one hour prior to physical activity to build up the body's stores of the ATP components.

The components of the liquid formulation do not need to be completely dissolved prior to consumption. That is, a minor portion of components may remain undissolved, and the liquid composition may be consumed in the form of a suspension, emulsion, or other non-homogeneous formulation. The amount of any such undissolved solids in the liquid formulation will generally be minimal and will not affect the efficacy of the liquid composition. Commercial packages of the composition will generally have a label with directions regarding recommended and maximum daily consumption guidelines.

A further aspect of the invention is directed to a nutraceutical liquid composition comprising, consisting of, or consisting essentially of:

a saccharide which is glucose or dextrose in the range of from about 15 to about 340 grams per liter of the liquid;
ribose in the range of from about 25 to about 85 grams per liter of the liquid;
coenzyme Q10 in the range of from about 15 milligrams to about 5 grams per liter of the liquid;
ATP disodium in the range of from about 15 milligrams to about 17 grams per liter of the liquid;
caffeine in the range of from about 415 milligrams to about 17 grams per liter of the liquid;
D-pinitol in the range of from about 15 milligrams to about 17 grams per liter of the liquid;
sodium in the range of from about 15 milligrams to about 5 grams per liter of the liquid;
potassium in the range of from about 15 milligrams to about 3.5 grams per liter of the liquid;
calcium in the range of from about 15 milligrams to about 2 grams per liter of the liquid;
magnesium in the range of from about 15 milligrams to about 2 grams per liter of the liquid;
a preservative;
an acidulant;
a flavoring agent;
a colorant; and
water or juice.

A further aspect of the invention is directed to an individual serving of a nutraceutical composition. The individual serving comprises, consists of, or consists essentially of:
  about 3 gm ribose;
  about 100 mg coenzyme Q10;
  about 250 mg adenosine triphosphate (ATP) disodium;
  about 70 mg caffeine;
  about 30 mg D-pinitol;
  about 12.5 gm dextrose or glucose;
  about 180 mg trisodium citrate;
  about 24 mg sodium benzoate;
  about 164 mg monopotassium phosphate;
  about 24 mg potassium sorbate;
  about 500 mg citric acid;
  about 215 mg calcium lactate;
  about 210 mg magnesium lactate;
  a flavoring agent; and
  a colorant.

The composition may be in the form of a tablet, powder, granulate, stick-pack, ready-to-dissolve concentrate, liquid concentrate, or a liquid formulation. When the composition is in the form of a solid or liquid concentrate, the composition is dissolved in an appropriate amount of water or other fluid to provide an individual serving of the ready-to-drink formulation.

A further aspect of the present invention is directed to an individual serving of a nutraceutical composition. The composition comprises, consists of, or consists essentially of:
  (a) about 3 gm ribose; about 100 mg coenzyme Q10; about 250 mg adenosine triphosphate (ATP) disodium; about 70 mg caffeine; about 30 mg D-pinitol; and about 12.5 gm dextrose or glucose; and
  (b) one or more components selected from the group consisting of:
  sodium in the range of from about 15 milligrams to about 5 grams per liter of a ready-to-drink aqueous formulation of the composition;
  potassium in the range of from about 15 milligrams to about 3.5 grams per liter of the ready-to-drink formulation;
  calcium in the range of from about 15 milligrams to about 2 grams per liter of the ready-to-drink formulation;
  magnesium in the range of from about 15 milligrams to about 2 grams per liter of the ready-to-drink formulation;
  a preservative, an acidulant, a flavoring agent, a colorant, and combinations thereof.

The composition may be formulated as an aqueous liquid, or in the form of a tablet, powder, granulate, stick-pack, or ready-to-dissolve solid or liquid concentrate.

III. DETAILED DESCRIPTION OF THE INVENTION

The composition and methods of the present invention are particularly suitable to anyone who engages in chronic physical activity, such as high-intensity and/or prolonged physical exercise.

Advantageously, the use of ribose in the novel composition facilitates generation of ATP, and enhances aerobic respiration utilization capacity. The ribose also attenuates muscle fatigue and decreases free radical formation during exercise. A preferred range of ribose in the inventive composition is about 25 to about 83.3 grams per liter. Ribose levels as high as 15 g per day can be safely ingested. Ribose has not been shown to have any lasting or damaging side effects during extended dosing regimens, though there are two known side effects of taking ribose in doses of 10 grams or more on an empty stomach. The first is transient hypoglycemia (low blood sugar) that can be eliminated by taking larger doses of ribose with other carbohydrates, as provided in the present invention. The second side effect that may occur in some individuals is gastrointestinal discomfort, including loose stools and diarrhea. Suitable forms of ribose include, but are not limited to, synthetically-made ribose extract from fermented yeast.

The carbohydrates in the inventive composition, specifically dextrose/glucose and ribose, provide a source of energy to extend exercise and improve performance of highly-intensive and/or prolonged physical activity. During exercise, glucose is needed to replace and increase muscle glycogen to prevent adverse effects of exercise on the body. A preferred range of dextrose or glucose or other saccharide in the composition is about 16.6 to about 333.3 grams per liter of prepared composition.

Exogenous administration of ATP increases vascular circulation to peripheral sites. Increased blood flow has a host of benefits, since blood is the delivery source of glucose, nutrients and oxygen for tissues. Research shows that ATP supplementation can elevate the body's extracellular ATP levels, making it effective for a variety of indications, such as energy, athletic performance and anti-aging. In fact, several published human studies in which ATP was administered intravenously have reported significant physiological and metabolic improvements. Pioneering animal studies have shown that chronic oral administration of ATP produces notable beneficial alterations in the host's physiology, including improvements in muscle metabolism, increases in peripheral blood flow and blood oxygenation. Research has also shown that when ATP disodium is taken orally, it enters the blood and creates a measurable increase in circulating ATP levels for at least six hours. A preferred range of ATP, in the form of the disodium salt, in the composition is about 1.6 to about 12.5 grams per liter of prepared composition.

ATP is not a stimulant. It does not affect heart rate nor does it increase blood pressure, and no adverse side effects have been observed in the pilot studies and human trials conducted with ATP disodium.

As used herein, the term "ATP" is intended to encompass any form of ATP unless otherwise qualified. The form of ATP in the inventive composition is not critical, and any convenient or commercially-available form of ATP can be used. For example, ATP may be in the form of the free compound, or in the form of a salt. Different forms of ATP may also be used in the compositions, such as a combination of the free compound and a salt of ATP. In one embodiment, ATP is in the form of an alkali metal salt, such as an ATP disodium salt. ATP disodium is available commercially and is generally produced through a proprietary fermentation process. When a different form of ATP is used other than ATP disodium, the amount of ATP to be added is to be adjusted on a mole basis so that the same molar amount is used.

D-Pinitol can facilitate the uptake of glucose into the skeletal muscle. D-pinitol is available commercially, and can be extracted from a number of plant sources, including alfalfa, Bougainvillea leaves, chickpeas, pine trees and soybeans. A preferred range of D-pinitol in the composition is about 250 milligrams to about 8.3 grams per liter of prepared composition.

Coenzyme Q10 (CoQ10) enhances ATP production and aerobic respiration utilization capacity, and attenuates muscle fatigue and decreases free radical formation during exercise. A preferred range of CoQ10 in the current composition is about 16.6 mg to about 5 grams per liter of prepared composition. CoQ10 has been shown to be safe and well tolerated at dosing levels as high as 3,000 mg per day over 8 months. In cardiovascular-related clinical trials encompassing 2,152 patients using 100 to 200 mg per day, CoQ10 has been shown to be safe, without any reports of toxicity or drug interactions. Less than one percent of CoQ10 users may experience gastrointestinal side effects such as nausea, vomiting, diarrhea, appetite suppression, heartburn, and epigastric discomfort. Suitable forms of Coenzyme Q10 include, but are not limited to, synthetically-made coenzyme Q10 extract including 10% CoQ10 Liposomes.

In addition to the components discussed above, the composition may further comprise electrolytes, minerals, and essential nutrients, such as but not limited to sodium, potassium, calcium and magnesium. The minerals and electrolytes provide essential nutrients for cellular and organ functions. They also attenuate muscle fatigue and delay the onset of exercise-associated muscle cramps during physical activity. Additionally, these electrolytes and minerals decrease cardiovascular and thermal strain and enhance exercise capacity in trained and untrained men and women. When sodium, potassium, calcium, and magnesium are included in the composition as electrolytes or minerals, preferred ranges of such substances in the composition are as follows:

sodium: about 16.6 mg to about 5 grams per liter;
potassium: about 16.6 milligrams to about 3.3 grams per liter;
calcium: about 16.6 milligrams to about 1.6 grams per liter; and
magnesium: about 16.6 milligrams to about 1.6 grams per liter.

Examples of suitable electrolytes include, but are not limited to, sodium chloride, sodium citrate, sodium benzoate, other sodium salts and mixtures thereof. Suitable sources of the minerals and electrolytes include, but are not limited to, biologically acceptable salts such as chlorides, sorbates, citrates, and the like, as well as mixtures thereof.

When the composition is sold in a ready-to-drink form, the liquid composition will be formulated to provide the components at a particular concentration. When the composition is sold as a liquid concentrate or powder, granulate or other solid, the package will contain instructions on how to reconstitute the beverage. For example, the package may state "Add to 12 oz. of water and shake well". The package may also contain additional information such as recommended or maximum daily consumption guidelines, nutritional information, and the like. In one embodiment, the ready-to-drink liquid formulation will be packaged in a container of approximately 60 ml. The containers may be disposable, although they are preferably recyclable or reusable. Unconsumed portions of the beverage may be discarded, or refrigerated for up to 3 days to maintain product quality. The composition can be marketed as individual servings, or as multi-serving packages, for example, containing two or more servings. The user would consume a single serving or portion, and then store or refrigerate the remainder for later consumption.

Any of the compositions may also optionally contain fruit juices, for example, lemon juice, orange juice, apple juice, grape juice, or pomegranate juice, to provide additional supplementation, nutrition, or enhanced taste. The amount of juice can range from about 0.1% to about 25% v/v of the compositions.

Although the solid and liquid concentrate compositions are intended for admixture with water, consistent with the invention, certain persons may wish to dissolve the composition in another liquid, such as juice or carbonated water.

As previously discussed, the composition within the scope of this invention may take a variety of forms. For instance, the composition may be manufactured and sold as a ready-to-drink liquid formulation. The present invention may also be prepared in concentrate or powder form to be reconstituted for use by the consumer by the addition of water or another liquid. Such reconstitution is to be made with the requisite amounts of water to ensure that the beverage contains the active components in the recommended proportions. In another embodiment, the freshly-prepared liquid may be prepared by the manufacturer or consumer and then frozen in individual servings. An individual serving of the frozen liquid can be defrosted and ingested by the consumer, or it may be eaten by the consumer as a frozen ice or similar novelty.

Preparation of the ready-to-drink liquid formulation comprising the inventive nutraceutical supplement composition is generally straightforward. In one embodiment, the liquid formulation can be prepared by mixing the ingredients using the following procedure.

(1) Preservatives are mixed with D-ribose, the saccharide, caffeine, and ATP disodium.
(2) CoQ10 is mixed with D-pinitol.
(3) If used, any electrolytes such as calcium, magnesium, potassium and sodium, as well as any flavoring agents or colorants, are mixed together.
(4) Items 1-3, are mixed and brought to solution in distilled water.
(5) An acidulant, such as citric acid, is added to the solution to adjust the pH to the desired level.
(6) The solution is packaged in a conventional aseptic bottle, can, brick-pack or other beverage container.

The process discussed above is merely illustrative, and other preparation sequences or procedures can be used. The liquid composition is made up using distilled, de-ionized or purified water, with a maximum calorie load of about 1,675 kcal/liter, optionally flavored with any choice of natural or synthetic fruit extract and/or aroma, such as pomegranate, gojiberry, blueberry, carrot, beet or others. The intended intake will normally be one 60 ml bottle per day, although dosing will depend on the concentration and amounts of the components in each serving.

As discussed, the composition described may be prepared and sold as a dry powder mixture for reconstitution by the consumer. The dry powder mixture can be prepared to provide a similar calorie load, flavoring, and coloring as the liquid ready-to-drink liquid. In this embodiment, the components of the nutraceutical composition are mixed in a conventional solids blending or mixing apparatus, and packaged into single-use portions, tablets, or other packages, or in bulk-sized multiple-portioned containers. A single unit package can be intended for dissolution in 50 or 100 ml of water or other liquid.

For improving physical and athletic performance, an average human need only ingest one serving per day of the liquid as described. Depending on the concentration of the liquid, in certain embodiments, more than one serving can be consumed. For optimal effects, the beverage can be consumed 30-45 minutes prior to physical activity, such as an athletic event or athletic training. Consumption of the liquid composition prior to athletic competition or other periods of strenuous activity will supply the body with electrolytes to buffer against negative effects of electrolyte loss lost during profuse sweating. The concentrations are merely indicative, and more concentrated or diluted drinks may be prepared using the same general formulation.

While the composition is not intended to be a pharmaceutical composition to treat medical conditions or diseases, the intake of the composition may help prevent negative effects of strenuous physical activity, such as fatigue, exhaustion, muscle cramps, etc. The present invention may also be beneficial for individuals who exhibit symptoms of fatigue including, but not limited to, those patients suffering from ischaemia, myoadenylate deaminase deficiency, AMP deaminase deficiency, congestive heart failure, chronic fatigue syndrome, fibromyalgia, and McArdle's disease.

The following examples further illustrate the nature of the present invention. The examples are by no means considered as restrictions or limitations of the present invention. For example, other components such as juices can be added to the composition to provide additional supplementation or flavoring.

EXAMPLE 1

Ready-to-drink Formulations

A liquid composition was prepared containing the following components for each 2 fluid ounces (60 ml) of liquid:

TABLE 1

| Ribose | 3 gm |
|---|---|
| Coenzyme Q10 | 100 mg |
| ATP disodium | 250 mg |
| Caffeine | 70 mg |
| D-Pinitol | 30 mg |
| Dextrose/glucose | 12.5 gm |
| Trisodium citrate | 180 mg |
| Sodium benzoate | 24 mg |
| Monopotassium phosphate | 164 mg |
| Potassium sorbate | 24 mg |
| Citric acid | 500 mg |
| Calcium lactate | 215 mg |
| Magnesium lactate | 210 mg |
| Deionized water | 48.14 gm |
| pH | 3.2-4.5 |
| *Citrus* punch flavoring | 22 mg |
| Food-grade colorant | 15 mg |

The liquid composition was prepared by mixing the ingredients in a specified order. (1) The preservatives (sodium benzoate and potassium sorbate) are mixed with D-ribose, caffeine, glucose and ATP disodium. (2) Coenzyme Q10 is mixed with D-pinitol. (3) The calcium, magnesium, potassium and sodium salts, and the remaining components (except citric acid) are mixed together. (4) Ingredients 1-3, are mixed and brought to solution in distilled water. (5) Citric acid is added to the solution to achieve pH=3.2-4.5. (6) The prepared solution is packaged in a conventional aseptic 2 fl. oz. bottle representing a single serving.

EXAMPLE 2

Stick-pack Units

Stick-packs containing the powdered nutraceutical composition were prepared by blending the following ingredients in a solids mixing apparatus using a wet-granulation or solid-granulation technique:

TABLE 2

| Ribose | 3 gm |
|---|---|
| Coenzyme Q10 | 100 mg |
| ATP disodium | 250 mg |
| Caffeine | 70 mg |
| D-Pinitol | 30 mg |
| Dextrose/glucose | 12.5 gm |
| Trisodium citrate | 180 mg |
| Sodium benzoate | 24 mg |
| Monopotassium phosphate | 164 mg |
| Potassium sorbate | 24 mg |
| Citric acid | 500 mg |
| Calcium lactate | 215 mg |
| Magnesium lactate | 210 mg |
| pH | 3.2-4.5 |
| *Citrus* punch flavoring | 22 mg |
| Food-grade colorant | 15 mg |

The blended powder was packaged into 3 stick-packs. Sufficient citric acid was included in the blended powder so that the reconstituted liquid composition would have a pH of 3.2 to 4.5. To prepare the liquid formulation, the contents of three single stick-packs are added to a 16.9 or 20 ounce-sized bottle of water to be consumed as a single serving. After shaking the bottle to dissolve or disperse the contents, the liquid composition is ready to consume. In an alternative embodiment, the formulation can be packaged into a single stick-pack, and the user would dissolve or dispense the contents of the stick-pack into 16.9 or 20 oz of water (or other fluid).

EXAMPLE 3

Tablets

Tablets containing the nutraceutical composition were prepared by blending the following ingredients in a solids mixing apparatus:

TABLE 3

| Ribose | 3 gm |
|---|---|
| Coenzyme Q10 | 100 mg |
| ATP disodium | 250 mg |
| Caffeine | 70 mg |
| D-Pinitol | 30 mg |
| Dextrose/glucose | 12.5 gm |
| Tri sodium citrate | 180 mg |
| Sodium benzoate | 24 mg |
| Monopotassium phosphate | 164 mg |
| Potassium sorbate | 24 mg |
| Citric acid | 500 mg |
| Calcium lactate | 215 mg |
| Magnesium lactate | 210 mg |
| pH | 3.2-4.5 |
| *Citrus* punch flavoring | 22 mg |
| Food-grade colorant | 15 mg |

Sufficient citric acid was added to the ingredients so that the reconstituted liquid would have a pH of 3.2-4.5. The blended powder was compressed using a tablet press to form two tablets. To prepare the liquid composition, two tablets are added to an 8-oz sized glass or bottle of water. After mixing or shaking the glass or bottle to dissolve or disperse the tablets, the liquid is ready to consume as a single serving. Dispersants, disintegrants, lubricants, or other typical tabletting excipients can be added to the tablet for facile tablet preparation or dissolution.

While the invention has been particularly shown and described with reference to particular embodiments, those skilled in the art will understand that various changes in form and details may be made without departing from the spirit and scope of the invention.

What is claimed is:

1. A nutraceutical liquid composition consisting of:
 a saccharide which is glucose or dextrose in the range of from about 15 to about 340 grams per liter of the liquid;
 ribose in the range of from about 25 to about 85 grams per liter of the liquid;
 coenzyme Q10 in the range of from about 15 milligrams to about 5 grams per liter of the liquid;
 ATP disodium in the range of from about 15 milligrams to about 17 grams per liter of the liquid;
 caffeine in the range of from about 415 milligrams to about 17 grams per liter of the liquid;
 D-pinitol in the range of from about 15 milligrams to about 17 grams per liter of the liquid;
 sodium in the range of from about 15 milligrams to about 5 grams per liter of the liquid;
 potassium in the range of from about 15 milligrams to about 3.5 grams per liter of the liquid;
 calcium in the range of from about 15 milligrams to about 2 grams per liter of the liquid;
 magnesium in the range of from about 15 milligrams to about 2 grams per liter of the liquid;
 a preservative;
 an acidulant;
 a flavoring agent;
 a colorant; and
 a liquid.

2. An individual serving of a nutraceutical composition consisting of:
 about 3 gm ribose;
 about 100 mg coenzyme Q10;
 about 250 mg adenosine triphosphate (ATP) disodium;
 about 70 mg caffeine;
 about 30 mg D-pinitol;
 about 12.5 gm dextrose or glucose;
 about 180 mg trisodium citrate;
 about 24 mg sodium benzoate;
 about 164 mg monopotassium phosphate;
 about 24 mg potassium sorbate;
 about 500 mg citric acid;
 about 215 mg calcium lactate;
 about 210 mg magnesium lactate;
 a flavoring agent; and
 a colorant,
 and optionally a liquid, one or more excipients, or both.

3. The composition according to claim 2, wherein the composition is formulated in a tablet, powder, granulate, stick-pack, ready-to-dissolve concentrate, liquid concentrate, or a liquid formulation.

4. An individual serving of a nutraceutical composition consisting of:
 (a) about 3 gm ribose; about 100 mg coenzyme Q10; about 250 mg adenosine triphosphate (ATP) disodium; about 70 mg caffeine; about 30 mg D-pinitol; and about 12.5 gm dextrose or glucose; and
 (b) one or more components selected from the group consisting of:
 sodium in the range of from about 15 milligrams to about 5 grams per liter of a ready-to-drink aqueous formulation of the composition;
 potassium in the range of from about 15 milligrams to about 3.5 grams per liter of the ready-to-drink formulation;
 calcium in the range of from about 15 milligrams to about 2 grams per liter of the ready-to-drink formulation;
 magnesium in the range of from about 15 milligrams to about 2 grams per liter of the ready-to-drink formulation;
 a preservative, an acidulant, a flavoring agent, a colorant, and combinations thereof, and optionally a liquid, one or more excipients, or both.

5. The composition according to claim 4, wherein the composition is formulated in an aqueous ready-to-drink liquid or a liquid concentrate for reconstitution with a liquid prior to consumption.

6. The composition according to claim 4, wherein the composition is formulated in a solid formulation for reconstitution by a consumer with a liquid prior to consumption.

7. The composition according to claim 1, wherein the liquid is water or juice.

8. A solid formulation comprising the composition according to claim 6, wherein the solid formulation is formulated in a tablet, powder, granulate, stick-pack, or ready-to-dissolve solid.

9. A solid formulation comprising the composition according to claim 4, wherein the solid formulation comprises one or more excipients.

10. An individual serving of a nutraceutical composition consisting of:
 3 gm ribose;
 100 mg coenzyme Q10;
 250 mg adenosine triphosphate (ATP) disodium;
 70 mg caffeine;
 30 mg D-pinitol;
 12.5 gm dextrose or glucose;
 180 mg trisodium citrate;
 24 mg sodium benzoate;
 164 mg monopotassium phosphate;
 24 mg potassium sorbate;
 500 mg citric acid;
 215 mg calcium lactate;
 210 mg magnesium lactate;
 a flavoring agent;
 a colorant, and optionally:
 water, juice, or both; and/or
 one or more excipients.

11. The composition according to claim 10, wherein the composition is formulated in a tablet, powder, granulate, stick-pack, ready-to-dissolve concentrate, or a liquid formulation.

12. An individual serving of a nutraceutical composition consisting of:
 (a) 3 gm ribose; 100 mg coenzyme Q10; 250 mg adenosine triphosphate (ATP) disodium; 70 mg caffeine; 30 mg D-pinitol; and 12.5 gm dextrose or glucose; and
 (b) one or more components selected from the group consisting of:
 sodium in the range of from 15 milligrams to 5 grams per liter of a ready-to-drink aqueous formulation of the composition;
 potassium in the range of from 15 milligrams to 3.5 grams per liter of the ready-to-drink formulation;
 calcium in the range of from 15 milligrams to 2 grams per liter of the ready-to-drink formulation;
 magnesium in the range of from 15 milligrams to 2 grams per liter of the ready-to-drink formulation;
 a preservative, an acidulant, a flavoring agent, a colorant, and combinations thereof; and
 optionally a liquid, one or more excipients, or both.

13. The composition according to claim 12, wherein the composition is formulated in an aqueous liquid or a liquid concentrate.

14. The composition according to claim 12, wherein the composition is formulated in a tablet, powder, granulate, stick-pack, or ready-to-dissolve concentrate.

\* \* \* \* \*